US011344624B2

(12) United States Patent
Kim

(10) Patent No.: US 11,344,624 B2
(45) Date of Patent: May 31, 2022

(54) MICROPARTICLES CONTAINING FINASTERIDE AND PREPARATION METHOD THEREOF

(71) Applicant: INVENTAGE LAB INC., Seongnam-si (KR)

(72) Inventor: Ju Hee Kim, Seongnam-si (KR)

(73) Assignee: INVENTAGE LAB INC., Seongnam-si (KR)

( * ) Notice: Subject to any disclaimer, the term of this patent is extended or adjusted under 35 U.S.C. 154(b) by 87 days.

(21) Appl. No.: 16/639,810

(22) PCT Filed: Aug. 17, 2018

(86) PCT No.: PCT/KR2018/009440
§ 371 (c)(1),
(2) Date: Feb. 18, 2020

(87) PCT Pub. No.: WO2019/035679
PCT Pub. Date: Feb. 21, 2019

(65) Prior Publication Data
US 2020/0246470 A1    Aug. 6, 2020

(30) Foreign Application Priority Data

Aug. 18, 2017  (KR) .......................... 10-2017-0104776
May 18, 2018  (KR) .......................... 10-2018-0057092

(51) Int. Cl.
*A61K 47/59*    (2017.01)
*A61K 9/50*     (2006.01)
(Continued)

(52) U.S. Cl.
CPC .......... *A61K 47/593* (2017.08); *A61K 9/5084* (2013.01); *A61K 31/56* (2013.01); *A61K 47/34* (2013.01)

(58) Field of Classification Search
None
See application file for complete search history.

(56) References Cited

U.S. PATENT DOCUMENTS 6,277,391 B1     8/2001 Seo et al.
2006/0014894 A1  1/2006 Torii et al.

FOREIGN PATENT DOCUMENTS

CN    1965839 A  *  5/2007
CN    1965839 A     5/2007
(Continued)

OTHER PUBLICATIONS

Takada, "Microfabrication-derived DDS: From batch to individual production", Drug Discovery & Therapeutics, 2 (3): 140-155 (Year: 2008).*

(Continued)

*Primary Examiner* — Isis A Ghali
(74) *Attorney, Agent, or Firm* — STIP Law Group, LLC

(57) ABSTRACT

The present invention relates to microparticles containing finasteride, as microparticles containing finasteride and a biodegradable polymer, in a form in which the microparticles have a shape in which the finasteride drug is uniformly distributed in spherical biodegradable polymer particles, and the microparticles have an average particle diameter of 20 to 70 μm.
The present invention relates to sustained-release microparticles which can maintain the effect of treating alopecia sustainably for 1 month to 3 months as the microparticles containing finasteride are administered, and a preparation method thereof, and
the present invention may facilitate storage and handling of microparticles containing finasteride unlike oral dosage forms as a patient need not directly store and handle the microparticles by using the microparticles containing finasteride in a manner that the microparticles are administered to (Continued)

the patient through injection, maintain the drug effect for a long period of time such as 1 month to 3 months, and facilitate the administration as an injection by decreasing a foreign body sensation and pain at the time of administering the injection to a patient as the particles are prepared to have the average diameter of the particles to a certain micro size.

10 Claims, 8 Drawing Sheets

(51) Int. Cl.
*A61K 31/56* (2006.01)
*A61K 47/34* (2017.01)

(56) References Cited

FOREIGN PATENT DOCUMENTS

| CN | 102631326 A | 8/2012 |
| CN | 103386118 A | 11/2013 |
| WO | WO2018088732 A1 | 5/2018 |

OTHER PUBLICATIONS

Goran T. Vladisavljevic et al, Glass capillary microfluidics for production of monodispersed poly (DL-lactic acid) and polycaprolactone microparticles: Experiments and numerical simulations, Journal of Colloid and Interface Science, Dec. 2013, vol. 418, pp. 163-170, Elsevier, Amsterdam, Netherlands.

International Search Report of PCT/KR2018/009440, dated Mar. 8, 2019, English translation.

Koji Kinoshita et al, From Single Microparticles to Microfluidic Emulsification: Fundamental Properties (Solubility, Density, Phase Separation) from Micropipette Manipulation of Solvent, Drug and Polymer Microspheres, Processes, Nov. 30, 2016, pp. 1-28, vol. 4, No. 49, MDPI, Basel, Switzerland.

Osama AA Ahmed et al, Finasteride-loaded biodegradable nanoparticles: Near-infrared quantification of plasma and prostate levels, Journal of Bioactive and Compatible Polymers, , 2017, pp. 1-11, vol. 32, No. 6, SAGE, Thousand Oaks, USA.

Luis V. Roque et al, Design of Finasteride-Loaded Nanoparticles for Potential Treatment of Alopecia, Skin Parmacology and Physiology, Jul. 8, 2017, pp. 197-204, vol. 30, KARGER, Basel, Switzerland.

\* cited by examiner

MICROPARTICLES CONTAINING FINASTERIDE AND PREPARATION METHOD THEREOF

CROSS-REFERENCE TO RELATED APPLICATIONS

This application is the U.S. National Phase under 35 U.S.C. § 371 of International Application No. PCT/KR2018/009440 filed on Aug. 17, 2018, which in turn claims the benefit of Korean Applications No. 10-2017-0104776, filed on Aug. 18, 2017, No. 10-2018-0057092, filed on May 18, 2018, the disclosures of which are incorporated by reference into the present application.

TECHNICAL FIELD

The present invention relates to microparticles containing finasteride and a preparation method thereof, and more particularly, to microparticles containing finasteride, which is a physiologically active substance for hair sprouting and hair growth, and a biodegradable polymer, and a preparation method thereof.

BACKGROUND ART

Therapeutic agents for male pattern alopecia currently used in Korea include finasteride and dutasteride as oral preparations. These therapeutic agents for alopecia suppress the production of a strong male hormone DHT by blocking 5-α-reductase inhibitors which act to convert testosterone into dihydrotestosterone (DHT) as the action mechanism illustrated in FIG. 1, and treat androgenetic alopecia by suppressing the shrinkage of hair roots by DHT at the scalp through the suppression of production of DHT.

5-α-reductase inhibitors can be divided into Type 1 and Type 2, and Type 1 is distributed in the scalp and sebaceous glands, and Type 2 is distributed in the scalp and prostate. Finasteride only blocks Type 2 of the 5-α-reductase inhibitor, but dutasteride blocks both Type 1 and Type 2 inhibitors. It is known that due to the mechanism, dutasteride is stronger than finasteride in terms of suppression effect of DHT. However, based on the first year of use, the expression rate of side effects of dutasteride was higher than that of finasteride, and finasteride is currently the most widely used as a therapeutic agent for alopecia and more advantageous than dutasteride in terms of safety due to the fact that finasteride is only approved by the FDA.

Existing oral therapeutic agents for alopecia such as Korean Patent Application Laid-Open No. 10-2016-0002411 can get therapeutic effects only when taken daily for 3 months or more, and have a problem in that when taking the medicine is stopped, the drug efficacy drops, thereby returning to the previous state. Accordingly, there is a problem in that in order to maintain the effect of treating alopecia by sustaining the drug efficacy, the medicine needs to be taken sustainably at a fixed time every day.

Therapeutic agents for alopecia such as dutasteride and finasteride are associated with male hormones, and thus are specified as a contraindication in pregnant or potentially pregnant women, and when the therapeutic agent for alopecia is exposed to pregnant or potentially pregnant women, the therapeutic agent may cause abnormalities of the external genitalia of a male fetus, so that the therapeutic agent for alopecia needs to be taken with caution in view of storage or handling of the therapeutic agents for alopecia because there is a risk of birth defects. Further, since the medicines are absorbed through the skin and may affect fetuses, there are problems in that the medicines need not be touched and medicine takers who live with pregnant or potentially pregnant women around the medicine takers need to handle the medicines with particular caution.

Therefore, there is an urgent need for developing a therapeutic agent for alopecia, which can maintain the drug efficacy for 1 month or more with one time administration and is conveniently stored and handled by using finasteride which is proved to be more stable as a therapeutic agent for alopecia.

DISCLOSURE

Technical Problem

The present invention relates to microparticles containing finasteride and a preparation method thereof.

An object of the present invention is to provide sustained-release microparticles capable of maintaining the effect of treating alopecia sustainably for 1 month to 3 months when the microparticles containing finasteride are administered, unlike oral dosage forms in the related art, which need to be taken daily due to the short half-life, and a preparation method thereof.

Another object of the present invention is to provide ease in storage and handling because microparticles containing finasteride are used in a manner that the microparticles are administered to a patient through injection so that the patient need not directly store and handle a medicine unlike oral dosage forms.

Still another object of the present invention is to maintain the effect of administering a drug for a long period of time such as 1 month to 3 months by using sustained-release particles containing finasteride, to, as an average diameter of particles is prepared to a constant micro size, maintain an effective drug concentration at a constant level by controlling the release of a drug from the microparticles, and to decrease a foreign body sensation and pain when the microparticles are applied to an injection consisting of particles with a uniform size and administered to a patient by the injection.

Technical Solution

To achieve the aforementioned objects, as a specific embodiment of the present invention, the present invention relates to microparticles containing finasteride, as microparticles containing finasteride and a biodegradable polymer, in which the microparticles have a shape in which the finasteride drug is uniformly distributed in spherical biodegradable polymer microparticles, and the microparticles have an average particle diameter of 20 to 70 μm.

As a specific embodiment of the present invention, the microparticles of the present invention may contain the biodegradable polymer and finasteride at a weight ratio of 4:1 to 15:1.

As a specific embodiment of the present invention, the microparticles of the present invention may release finasteride sustainably for 1 month to 3 months.

As a specific embodiment of the present invention, the biodegradable polymer of the present invention is selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide) (PLGA), but the biodegradable polymer is not limited to the example.

As a specific embodiment of the present invention, the microparticles of the present invention are prepared by using a microchannel, and a width (w) of the cross section of the channel is within a ratio range of 0.7 to 1.3 for an average diameter (d') of the microparticles.

As a specific embodiment of the present invention, the microparticles of the present invention are prepared by using a microchannel, and a height (d) of the cross section of the channel is within a ratio range of 0.7 to 1.3 for an average diameter (d') of the microparticles.

As a specific embodiment of the present invention, a composition for treating and preventing alopecia and promoting hair sprouting of the present invention contains the microparticles.

As an exemplary embodiment of the present invention, the present invention relates to a method for preparing microparticles containing finasteride, the method including: 1) preparing a first mixture by dissolving a biodegradable polymer and finasteride in an organic solvent; 2) preparing a second mixture by dissolving a surfactant in water; 3) infusing the first mixture in Step 1) into a microchannel in a straight-line direction and allowing the first mixture to flow; 4) preparing microparticles in which finasteride is uniformly distributed in spherical biodegradable polymer particles by infusing the second mixture in Step 2) into a microchannel formed on both side surfaces or one side surface thereof and allowing the second mixture to flow such that the first mixture in Step 3) can form an intersection point with a microchannel flowing in a straight-line direction, and intersecting a flow of the first mixture in a straight-line direction with a flow of the second mixture; 5) collecting the microparticles produced at the intersection point in Step 4); 6) evaporating and removing an organic solvent present in the microparticles by stirring the microparticles collected in Step 5); and 7) washing the microparticles in Step 6) and drying the microparticles, in which the microparticles have an average particle diameter of 20 to 70 μm.

As a specific embodiment of the present invention, the first mixture in Step 1) of the present invention may include a biodegradable polymer in an amount of 10 to 20 wt %.

As a specific embodiment of the present invention, the first mixture in Step 1) of the present invention may contain the biodegradable polymer and finasteride at a weight ratio of 4:1 to 15:1.

As a specific embodiment of the present invention, the biodegradable polymer of the present invention is selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide) (PLGA), but the biodegradable polymer is not limited to the example.

As a specific embodiment of the present invention, the organic solvent in Step 1) of the present invention is one or more selected from the group consisting of dichloromethane, chloroform, chloroethane, dichloroethane, trichloroethane, and a mixture thereof.

As a specific embodiment of the present invention, the second mixture in Step 2) of the present invention may include a surfactant in an amount of 0.2 wt % to 0.3 wt %.

As a specific embodiment of the present invention, the surfactant in Step 2) of the present invention is one or more selected from the group consisting of a non-ionic surfactant, an anionic surfactant, a cationic surfactant, and a mixture thereof.

As a specific embodiment of the present invention, Step 3) of the present invention may infuse the first mixture into a microchannel in a straight-line direction under a pressure of 600 to 1,000 mbar.

As a specific embodiment of the present invention, Step 4) of the present invention may infuse the second mixture into a microchannel formed on both side surfaces or one side surface so as to form an intersection point with a microchannel through which the first mixture flows in a straight-line direction, and may infuse the second mixture under a pressure of 1,200 to 1,600 mbar.

As a specific embodiment of the present invention, Step 5) of the present invention may collect microparticles in a bath comprising a mixed solution comprising a surfactant in an amount of 0.2 wt % to 0.3 wt %.

As a specific embodiment of the present invention, Step 6) of the present invention may include: Step 6-1) firstly stirring the microparticles at a rate of 800 to 1,200 rpm at 14 to 16° C. for 1 to 2 hours; Step 6-2) secondly stirring the microparticles at a rate of 800 to 1,200 rpm at 19 to 21° C. for 0.5 to 1.5 hours after the first stirring; and Step 6-3) thirdly stirring the microparticles at a rate of 800 to 1200 rpm at 24 to 26° C. for 0.5 to 1.5 hours after the second stirring.

As a specific embodiment of the present invention, the microchannels in Steps 3) and 4) of the present invention are formed on a surface of a wafer, and an average diameter of the microchannels is 40 to 100 μm, preferably 40 to 60 μm, and more preferably 50 μm, but is not limited to the example.

Advantageous Effects

The present invention relates to microparticles containing finasteride and a preparation method thereof, and more particularly to sustained-release microparticles which can maintain the effect of treating alopecia sustainably for 1 month to 3 months as the microparticles containing finasteride are administered, and a preparation method thereof.

Further, the present invention may facilitate storage and handling of microparticles containing finasteride unlike oral dosage forms as a patient need not directly store and handle the microparticles by using the microparticles containing finasteride in a manner that the microparticles are administered to the patient through injection, maintain the drug effect for a long period of time such as 1 month to 3 months, and facilitate the administration as an injection by decreasing a foreign body sensation and pain at the time of administering the injection to a patient as the particles are prepared by maintaining the average diameter of the particles to a certain micro size.

BEST MODE

According to an exemplary embodiment of the present invention, the present invention relates to microparticles containing finasteride, which are microparticles containing finasteride and a biodegradable polymer, in which the microparticles have a shape in which the finasteride drug is uniformly distributed in the spherical biodegradable polymer, and the microparticles have an average particle diameter of 20 to 70 μm.

According to another exemplary embodiment of the present invention, the present invention relates to a method for preparing microparticles containing finasteride, the method including: 1) preparing a first mixture by dissolving a biodegradable polymer and finasteride in an organic solvent; 2) preparing a second mixture by dissolving a surfactant in water; 3) infusing the first mixture in Step 1) into a microchannel in a straight-line direction and allowing the first mixture to flow; 4) preparing microparticles in a form in which a finasteride drug is uniformly distributed in spherical biodegradable polymer particles by infusing the second mixture in Step 2) into a microchannel formed on both side surfaces or one side surface and allowing the second mixture to flow so as to form an intersection point with a microchannel through which the first mixture in Step 3) flows in a straight-line direction, and intersecting a flow of the first mixture in a straight-line direction with a flow of the second mixture; 5) collecting the microparticles produced at the intersection point in Step 4); 6) evaporating and removing an organic solvent present in the microparticles collected in Step 5) by stirring the microparticles; and 7) washing the microparticles in Step 6) and drying the microparticles, in which the microparticles have an average particle diameter of 20 to 70 μm.

MODE FOR INVENTION

Hereinafter, the Examples of the present invention will be described in detail such that a person skilled in the art to which the present invention pertains can easily carry out the present invention. However, the present invention can be implemented in various different forms, and is not limited to the Examples described herein.

Figure 1:
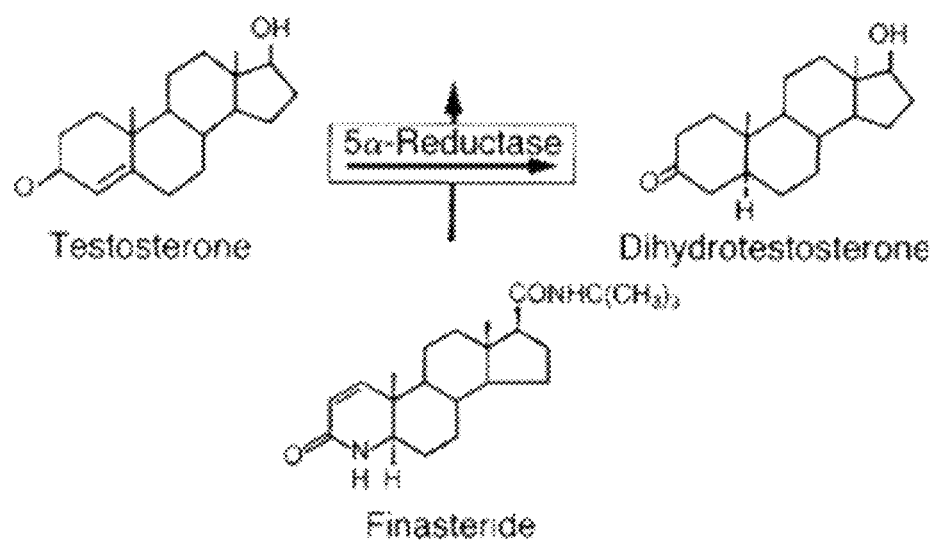
FIG. 1 is an action mechanism of a therapeutic agent for alopecia.
Figure 2:
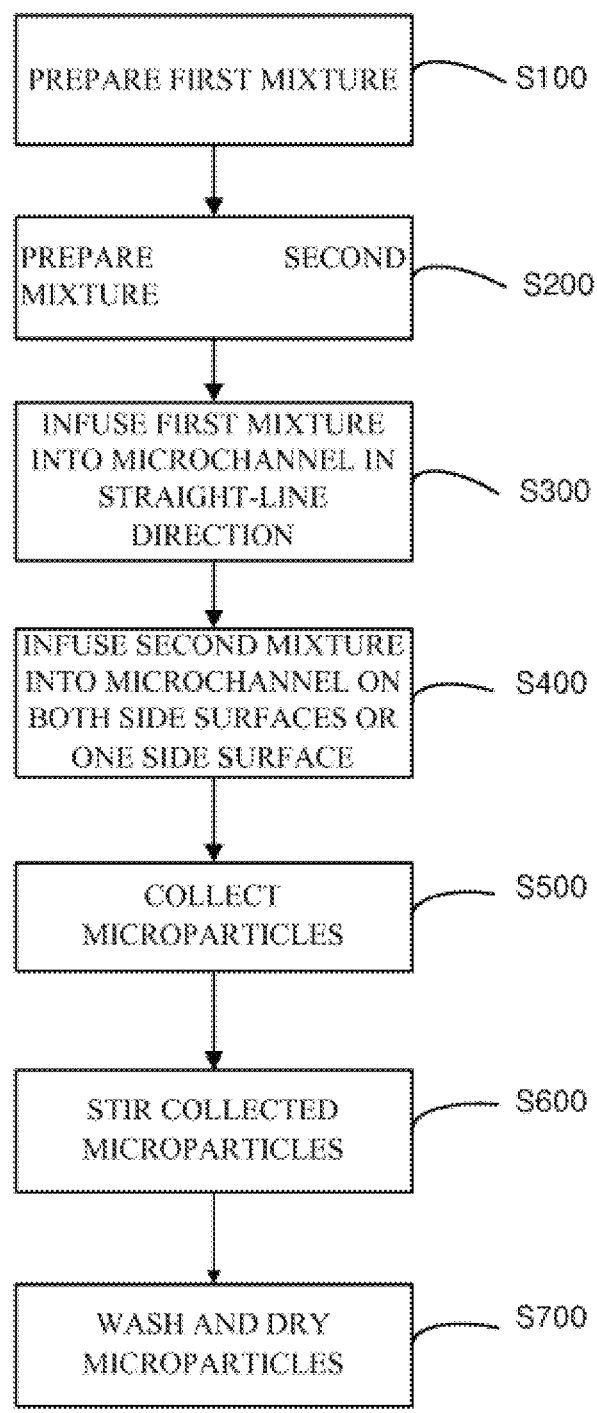
FIG. 2 is a flowchart of a method for preparing microparticles containing finasteride of the present invention.

FIG. 2 is a flowchart of a method for preparing microparticles containing finasteride of the present invention.

According to the aforementioned flowchart, the preparation of the microparticles containing finasteride of the present invention proceeds in the order of 1) preparing a first mixture (S100); 2) preparing a second mixture (S200); 3) infusing the first mixture into a microchannel in a straight-line direction (S300); 4) infusing the second mixture into a microchannel on both side surfaces or one side surface (S400); collecting the microparticles (S500); stirring the collected microparticles (S600); and washing the microparticles and drying the microparticles (S700).

More specifically, a method for preparing microparticles containing finasteride according to an exemplary embodiment of the present invention will be described as follows.

Step 1) (S100) is a step of preparing a first mixture, specifically a step of preparing a first mixture by dissolving a biodegradable polymer and finasteride in an organic solvent, in which the biodegradable polymer is selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof, and is preferably poly(lactide-co-glycolide) (PLGA), but the biodegradable polymer is not limited to the example.

Further, the organic solvent is an organic solvent which is immiscible with water, is one or more selected from the group consisting of, for example, chloroform, chloroethane, dichloroethane, trichloroethane, and a mixture thereof, and is preferably dichloromethane, but the organic solvent is not limited to the example, and the organic solvent can dissolve a biodegradable polymer and finasteride, and the organic solvent is not limited to the aforementioned example but any organic solvent can be easily selected by a person with ordinary skill in the art.

Step 1) (S100) prepares a first mixture in which a biodegradable polymer and finasteride are dissolved, and as the solvent, an organic solvent is used as described above. The finasteride and the biodegradable polymer are completely dissolved by using an organic solvent using dissolution characteristics of the finasteride and the biodegradable polymer. After the finasteride and the biodegradable polymer are completely dissolved, the first mixture contains the biodegradable polymer and finasteride at a weight ratio of 4:1 to 15:1.

When the weight ratio of the biodegradable polymer and finasteride is less than 4:1, that is, when the biodegradable polymer is contained at less than the above weight ratio, the weight ratio of the biodegradable polymer is smaller than the weight ratio of finasteride, so that there occurs a problem in that it is difficult to prepare microparticles in a form in which finasteride is uniformly distributed and contained in the spherical biodegradable polymer particles, and when the weight ratio of the biodegradable polymer and finasteride is more than 15:1, that is, when the biodegradable polymer is contained at more than the above weight ratio, the content of finasteride in the microparticles is small, so that there occurs a problem in that the microparticles need to be administered in a large amount in order to administer the drug at a desired concentration.

More specifically, the biodegradable polymer is comprised in an amount of 10 to 20 wt %, preferably 15 wt % in the first mixture, but the amount is not limited to the example.

Step 2) (S200) is a step of preparing a second mixture, and prepares a second mixture by dissolving a surfactant in water. The surfactant can be used without limitation as long as the surfactant can help the biodegradable polymer solution form a stable emulsion. Specifically, the surfactant is one or more selected from the group consisting of a nonionic surfactant, an anionic surfactant, a cationic surfactant, and a mixture thereof, and more specifically, the surfactant is one or more selected from the group consisting of methyl cellulose, polyvinylpyrrolidone, lecithin, gelatin, polyvinyl alcohol, polyoxyethylene sorbitan fatty acid esters, polyoxyethylene castor oil derivatives, sodium lauryl sulfate, sodium stearate, esters, amines, linear diamines, fatty amines, and a mixture thereof, and is preferably polyvinyl alcohol, but the surfactant is not limited to the example.

Step 3) (S300) and Step 4) (S400) are steps of infusing the first mixture and the second mixture into a microchannel formed on a wafer and allowing the first mixture and the second mixture to flow.

More specifically, aluminum is deposited onto a silicon wafer by using an e-beam evaporator, and a photoresist is patterned on aluminum by using a photolithography technique. Thereafter, the wafer is aluminum-etched by using a photoresist as a mask, silicon is etched by deep ion reactive etching (DRIE) by using aluminum as a mask after removing the photoresist, and glass is anodically bonded onto the wafer and hermetically sealed after removing aluminum, thereby manufacturing the aforementioned microchannel.

Further, the aforementioned microchannels have an average diameter of 40 to 100 μm, preferably 40 to 60 μm, and more preferably 50 μm, but the average diameter is not limited to the example. When the microchannels have an average diameter of 40 μm or less, microparticles to be prepared are likely to be prepared as small microparticles having a diameter of 20 μm or less, so that the microparticles are highly likely to be captured by microphages after being infused into the human body, and through this, it is possible to affect the release and in vivo absorption of an effective drug. In addition, when the channels have an average diameter of 100 μm or more, microparticles to be prepared are likely to be prepared as microparticles having a size of 70 μm or more, so that when the injection is administered, a foreign body sensation and pain may be increased, and the particle size distribution of the prepared particles is increased, so that it is difficult to prepare microparticles having a uniform particle size.

Figure 8:
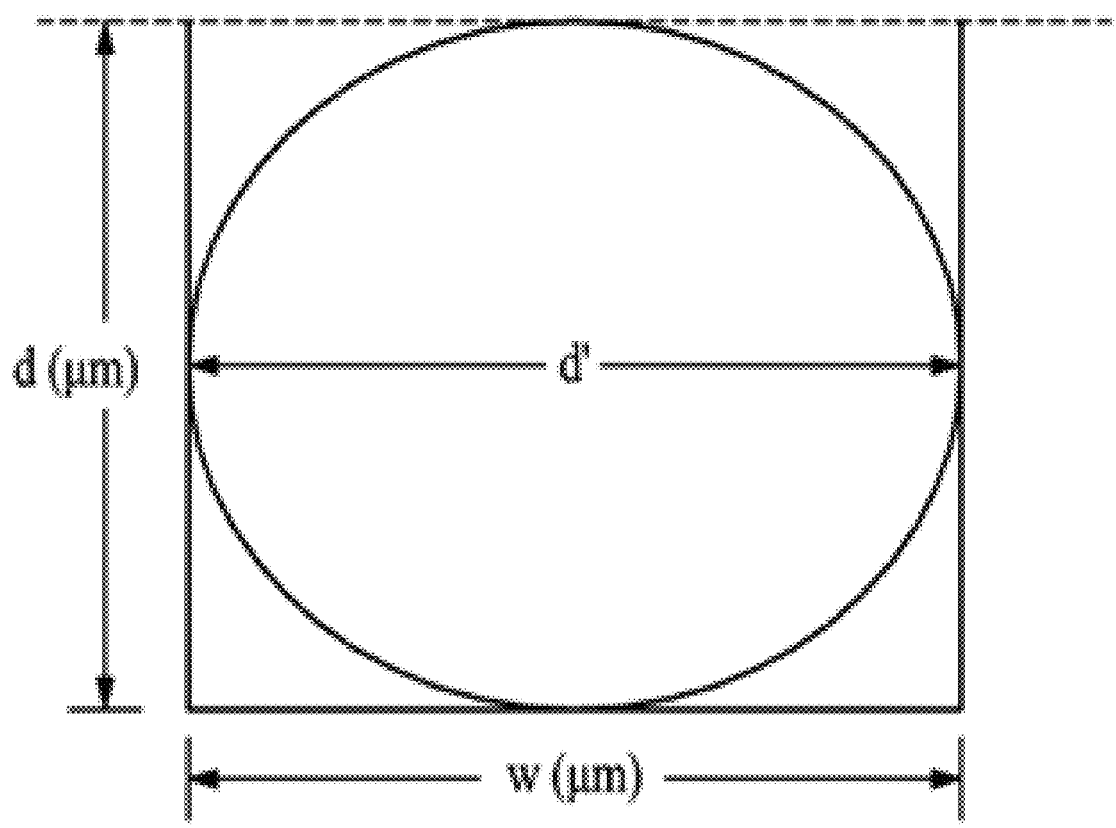
FIG. 8 is a view on the relationship between an average diameter of microparticles and a cross-section of a microchannel.

In addition, a width (w) of the cross section and a height (d) of the cross section of the microchannel are closely associated with an average diameter (d') of microparticles to be prepared. As in FIG. 8, the width (w) of the cross section of the microchannel is within a ratio range of 0.7 to 1.3 for an average diameter (d') of the microparticles, and a height (d) of the cross section of the microchannel is within a ratio range of 0.7 to 1.3 for an average diameter (d') of the microparticles.

That is, when the average diameter (d') of the microparticles to be prepared is determined, it is possible to prepare microparticles with a desired size only when the width (w) and height (d) of the cross section of the microchannel are set to a ratio range of 0.7 to 1.3 for the d'.

Step 3) (S300) infuses the first mixture into a microchannel in a straight-line direction and allows the first mixture to flow, and Step 4) (S400) infuses the second mixture into a microchannel on both side surfaces or one side surface formed so as to form an intersection point with a microchannel in a straight-line direction, and allows the second mixture to flow.

That is, the first mixture flows along the microchannel in a straight-line direction, and the second mixture flows along the microchannel which forms an intersection point with the microchannel in a straight-line direction on both side surfaces or one side surface based on the microchannel in a straight-line direction, and meets the flow of the first mixture.

In this case, when the first mixture is infused into a microchannel in a straight-line direction, the first mixture is infused under a certain pressure condition and allowed to flow at a certain flow rate, and in this case, the pressure condition is 600 to 1,000 mbar, preferably 800 mbar, but is not limited to the example. Further, when the second mixture is infused into a microchannel on both side surfaces or one side surface, the second mixture is infused under a certain pressure condition and allowed to flow at a certain flow rate, and in this case, the pressure condition is 1,200 to 1,600 mbar, preferably 1,400 mbar, but is not limited to the example.

That is, in order to allow the second mixture forming an intersection point with the flow of the first mixture to flow at a faster flow rate than the first mixture to be infused into the microchannel in a straight-line direction, the second mixture is allowed to flow under a higher pressure condition.

As described above, the second mixture having a relatively faster flow rate compresses the first mixture at a point where the flow of the first mixture and the flow of the second mixture meet each other by varying the flow rates of the first mixture and the second mixture and making the flow rate of the second mixture faster than the flow rate of the first mixture, and in this case, due to repulsive force between the first mixture and the second mixture, the biodegradable polymer and finasteride in the first mixture form spherical microparticles, and more specifically, microparticles in a form in which finasteride is uniformly distributed in the spherical biodegradable polymer are formed.

Step 5) (S500) is a step of collecting microparticles, and prevents aggregation of initially produced microparticles by collecting the microparticles in a bath comprising the second mixture.

Step 5) (S500) uses the second mixture prepared in Step 2) (S200), that is, a mixed solution of a surfactant and water, and is used to prevent aggregation of collected microparticles by preparing the second mixture in Step 2) (S200), and then infusing a portion of the second mixture into a microchannel, and transferring the other portion to the bath in Step 5) (S500).

Step 6) (S600) is a step of stirring microparticles collected in the bath, and an organic solvent present on the surfaces of the microparticles is evaporated and removed by stirring the microparticles at a predetermined stirring rate under a predetermined temperature condition. In this case, the stirring condition proceeds in an order of firstly stirring the microparticles at a rate of 800 to 1,200 rpm at 14 to 16° C. for 1 to 2 hours; secondly stirring the microparticles at a rate of 800 to 1,200 rpm at 19 to 21° C. for 0.5 to 1.5 hours after the first stirring; and thirdly stirring the microparticles at a rate of 800 to 1,200 rpm at 24 to 26° C. for 0.5 to 1.5 hours after the second stirring. The stirring rate is 800 to 1,200 rpm, preferably 1,000 rpm, but is not limited to the example. The stirring rate at which microparticles are stirred is maintained equally in the first, second, and third stirring, but the microparticles are stirred while gradually increasing the temperature, and as the temperature is increased step by step, the evaporation rate of the organic solvent present on the surfaces of the microparticles may be adjusted. That is, microparticles having smooth surfaces may be prepared by slowly evaporating the organic solvent present on the surfaces of the microparticles.

More specifically, in Step 6) (S600), the microparticles are firstly stirred at 14 to 16° C. for 1 to 2 hours, preferably at 15° C. for 1.5 hours. Thereafter, the microparticles are secondly stirred at 19 to 21° C. for 0.5 to 1.5 hours, preferably at 20° C. for 1 hour. Thereafter, the microparticles are thirdly stirred at 24 to 26° C. for 0.5 to 1.5 hours, preferably at 25° C. for 1 hour.

The temperature at which the first mixture and the second mixture flow in the microchannel is also 14 to 16° C., preferably 15° C. That is, after the mixtures flow in the microchannel and form an intersection point to produce microparticles, the temperature is constantly maintained at a low temperature of 14 to 16° C. until the collected microparticles are firstly stirred. Only when the low temperature is maintained during the process of preparing microparticles, it is possible to prepare and maintain spherical particles. That is, when the temperature is not under the low temperature condition, there occurs a problem in that it is difficult to prepare particles having a predetermined spherical shape.

Finally, Step 7) (S700) is a step of washing the microparticles and drying the microparticles, and the microparticles from which the organic solvent on the surfaces is completely removed by stirring are washed several times with purified water which is sterilized and filtered to remove the surfactant remaining in the microparticles, and are later lyophilized.

The microparticles finally produced are in a form in which the finasteride drug is uniformly distributed in the spherical biodegradable polymer microparticles, have an average particle diameter of 20 to 70 μm, and contain the biodegradable polymer and finasteride at a weight ratio of 3:1 to 9:1. When the microparticles have an average diameter of less than 20 μm, the microparticles are highly likely to be captured by macrophages after being infused into the human body, and accordingly, the release of the drug from the particles and in vivo absorption of the drug may be affected, and when the particles have an average diameter of more than 70 μm, pain may be increased when the drug included in an injection is administered to a patient to be administered by using a syringe needle having a large gauge.

The weight ratio of the biodegradable polymer and finasteride included in the microparticles is the same as the weight ratio in the first mixture, and as the microparticles are prepared and the organic solvent is completely evaporated and removed, it is possible to prepare microparticles containing the biodegradable polymer and finasteride at a ratio which is the same as the weight ratio in the first mixture.

Example 1

Preparation of Microparticles Containing Finasteride

A first mixture was prepared by dissolving poly(lactide-co-glycolide) (PLGA) and finasteride in dichloromethane. In this case, poly(lactide-co-glycolide) in the first mixture was contained at a ratio of 15 wt %, and the weight ratio of poly(lactide-co-glycolide) and finasteride was 4:1.

A second mixture including polyvinyl alcohol in an amount of 0.25 wt % was prepared by mixing a surfactant polyvinyl alcohol with water.

The first mixture and the second mixture were infused into a microchannel formed on a silicon wafer and allowed to flow. In this case, in order to allow the first mixture and the second mixture to flow at a certain flow rate, the first mixture and the second mixture were allowed to flow under a pressure condition of 800 mbar and under a pressure condition of 1,400 mbar, respectively. The temperature condition was maintained at 15° C.

Microparticles produced at an intersection point where the flow of the first mixture and the flow of the second mixture meet each other were collected in a bath comprising the second mixture. The microparticles collected in the bath were firstly stirred at a rate of 1,000 rpm at 15° C. for 1.5 hours, the temperature was increased to 20° C. and the microparticles were secondly stirred at a rate of 1,000 rpm for 1 hour, and the temperature was increased to 25° C. and the microparticles were thirdly stirred at a rate of 1,000 rpm for 1 hour.

The microparticles completely stirred were washed several times with purified water which was sterilized and filtered, and were lyophilized, thereby preparing microparticles.

Example 2

Microparticles were prepared in the same manner as in Example 1, except that poly(lactide-co-glycolide) and finasteride were contained at a weight ratio of 9:1.

Example 3

Microparticles were prepared in the same manner as in Example 1, except that poly(lactide-co-glycolide) and finasteride were contained at a weight ratio of 2:1.

Example 4

Microparticles were prepared in the same manner as in Example 1, except that poly(lactide-co-glycolide) and finasteride were contained at a weight ratio of 12:1.

Example 5

Microparticles were prepared in the same manner as in Example 1, except that poly(lactide-co-glycolide) and finasteride were contained at a weight ratio of 15:1.

Example 6

Microparticles were prepared in the same manner as in Example 1, except that poly(lactide-co-glycolide) and finasteride were contained at a weight ratio of 20:1.

Examples 7 to 11

Microparticles were prepared in the same manner as in Example 1, but microparticles were collected in the bath comprising the second mixture, and then the stirring process was performed under the conditions in the following Table 1 as the stirring conditions.

TABLE 1

|  | Stirring condition | Stirring temperature | Stirring time | Stirring rate |
| --- | --- | --- | --- | --- |
| Example 7 | 1 | 15° C. | 1.5 hours | 800 rpm |
|  | 2 |  | 1 hour | 1,000 rpm |
|  | 3 |  | 1 hour | 1,200 rpm |
| Example 8 | 1 | 20° C. | 1.5 hours | 800 rpm |
|  | 2 |  | 1 hour | 1,000 rpm |
|  | 3 |  | 1 hour | 1,200 rpm |
| Example 9 | 1 | 25° C. | 1.5 hours | 800 rpm |
|  | 2 |  | 1 hour | 1,000 rpm |
|  | 3 |  | 1 hour | 1,200 rpm |
| Example 10 | 1 | 15° C. | 1.5 hours | 800 rpm |
|  | 2 | 20° C. | 1 hour |  |
|  | 3 | 25° C. | 1 hour |  |
| Example 11 | 1 | 15° C. | 1.5 hours | 1,200 rpm |
|  | 2 | 20° C. | 1 hour |  |
|  | 3 | 25° C. | 1 hour |  |

Experimental Example 1

Drug Release Experiment of Microparticles Containing Finasteride

1. In-Vivo PK

About 100 mg of the microparticles in Examples 1 to 6 were put into a glass test container having a volume of 120 mL, and the container was filled with 100 mL of a release test solution. A drug release experiment was performed by putting the test container into a water bath at 45° C. and reciprocating the test container at an amplitude of 4 cm and a shaking frequency of 120 times/min as an experimental condition for acceleration of drug release. At the time of collecting the sample, the mixture was mixed by shaking the bottle well, and 1 mL of the sample was taken. After the sample was centrifuged at 13,000 rpm for 3 minutes, the supernatant was taken and analyzed with high performance liquid chromatography.

The drug release experimental results are shown in the following Table 2 and FIG. 3.

TABLE 2

| Day | Example 1 | Example 2 | Example 3 | Example 4 | Example 5 | Example 6 |
|---|---|---|---|---|---|---|
| 0 | 0 | 0 | 0 | 0 | 0 | 0 |
| 0.02 | 32.60 | 27.85 | 35.00 | 16.40 | 15.30 | 5.49 |
| 0.04 | 38.83 | 30.73 | 40.3 | 18.6 | 17.32 | 6.53 |
| 0.06 | 44.97 | 39.6 | 47.1 | 20.4 | 20.6 | 7.49 |
| 0.08 | 42.47 | 23.4 | 50.3 | 21.6 | 21.7 | 8.51 |
| 0.10 | 46.80 | 28.80 | 50.40 | 22.00 | 21.90 | 8.70 |
| 0.13 | 50.53 | 32.53 | 53.70 | 24.50 | 23.70 | 9.42 |
| 0.17 | 47.03 | 33.67 | 65.80 | 22.80 | 22.75 | 10.42 |
| 0.25 | 62.60 | 29.53 | 70.60 | 25.00 | 24.64 | 12.24 |
| 0.33 | 50.93 | 29.03 | 76.30 | 21.60 | 25.86 | 12.12 |
| 0.50 | 35.67 | 17.27 | 65.20 | 20.70 | 26.75 | 13.24 |
| 1.00 | 23.40 | 12.38 | 51.80 | 18.40 | 23.46 | 11.05 |
| 7 | 33.27 | 9.13 | 35.70 | 16.70 | 22.45 | 15.64 |
| 14 | 20.50 | 25.73 | 25.73 | 14.90 | 20.71 | 16.50 |
| 21 | 24.00 | 33.63 | 0.00 | 15.40 | 20.66 | 20.21 |
| 28 | 2.78 | 20.03 | 0.00 | 13.90 | 18.21 | 31.62 |
| 35 | 0.00 | 16.50 | 0.00 | 16.42 | 17.55 | 24.34 |
| 42 | 0.00 | 15.80 | 0.00 | 17.56 | 17.21 | 25.71 |
| 49 | 0.00 | 10.47 | 0.00 | 15.63 | 16.43 | 26.46 |
| 56 | 0.00 | 9.51 | 0.00 | 13.85 | 14.59 | 22.43 |
| 63 | 0.00 | 8.71 | 0.00 | 13.54 | 13.84 | 20.87 |
| 70 | 0.00 | 8.59 | 0.00 | 10.63 | 12.54 | 20.67 |
| 77 | 0.00 | 6.53 | 0.00 | 8.21 | 10.62 | 18.51 |
| 84 | 0.00 | 5.49 | 0.00 | 7.58 | 8.53 | 17.05 |
| 91 | 0.00 | 1.54 | 0.00 | 6.42 | 6.19 | 15.59 |

Figure 3:
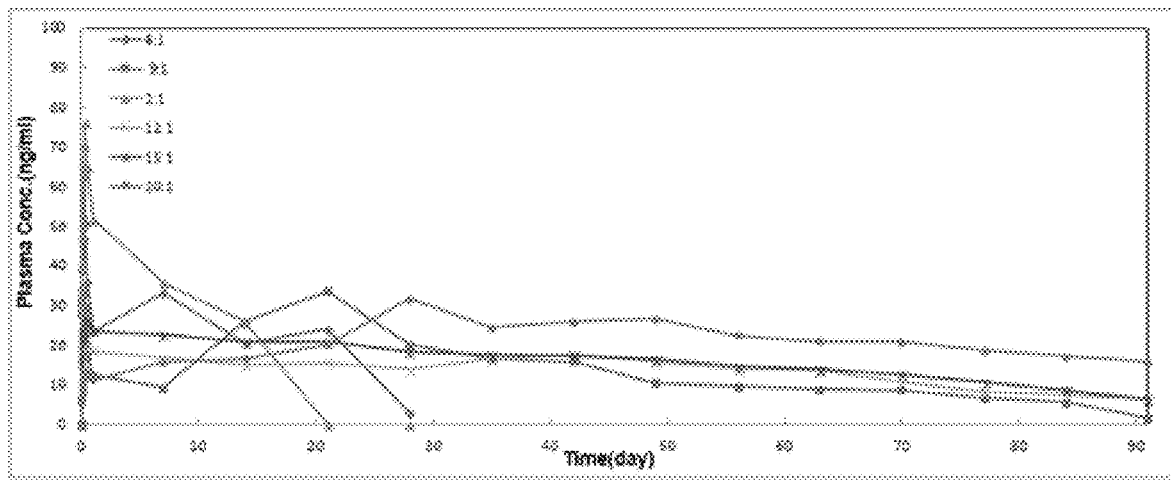
FIG. 3 is a graph of results for the drug release period according to the weight ratio of a biodegradable polymer and finasteride of the present invention.

(Unit ng/ml) According to FIG. 3 and Table 2, there are problems in that in Example 3, an excessively large amount of drug was released at the initial stage, and after 14 days, the drug was almost completely released, and accordingly, it was difficult to exhibit an effect of releasing the drug over a long period of time. In addition, in Example 6, there is a problem in that the amount of drug released at the initial stage was so small that the treatment effect of the finasteride drug was slight.

On the contrary, in Example 1, it was confirmed that the finasteride drug was released sustainably for 1 month, and in Examples 2, 4, and 5, it was confirmed that the finasteride drug was released sustainably up to 3 months.

Experimental Example 2

Study on Shapes of Microparticles

In order to study the shapes of microparticles according to the stirring conditions, the shapes of the microparticles prepared under the conditions in Examples 1 and 5 to 10 were studied through SEM photographs.

The results are shown in the following Table 3.

TABLE 3

| Experiment according to stirring condition | Preparation result of microparticles |
|---|---|
| Example 7 | Δ |
| Example 8 | Δ |
| Example 9 | Δ |
| Example 10 | ○ |
| Example 11 | ○ |
| Example 1 | ○ |

Figure 4:
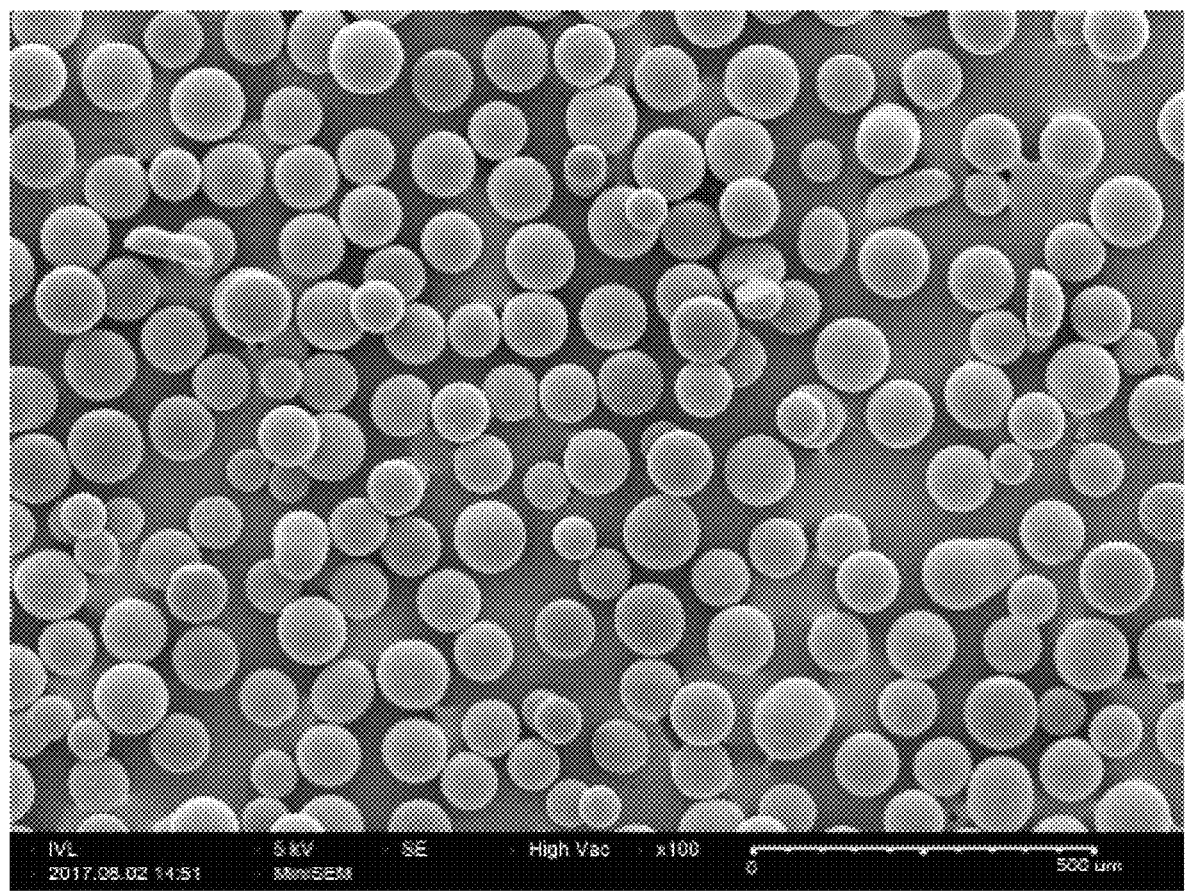
FIG. 4 is an SEM photograph of microparticles by the preparation method according to an exemplary embodiment of the present invention.
Figure 5:
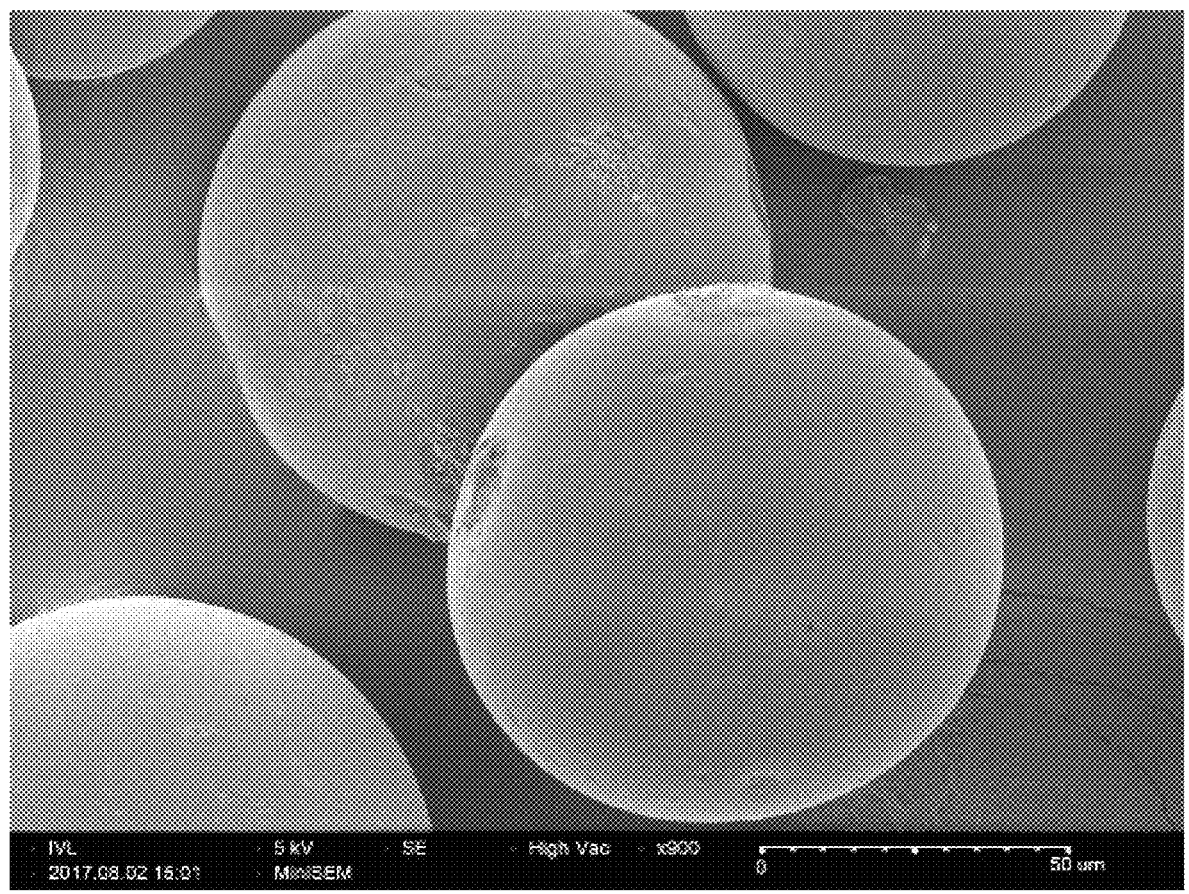
FIG. 5 is an SEM photograph of microparticles by the preparation method according to an exemplary embodiment of the present invention.
Figure 6:
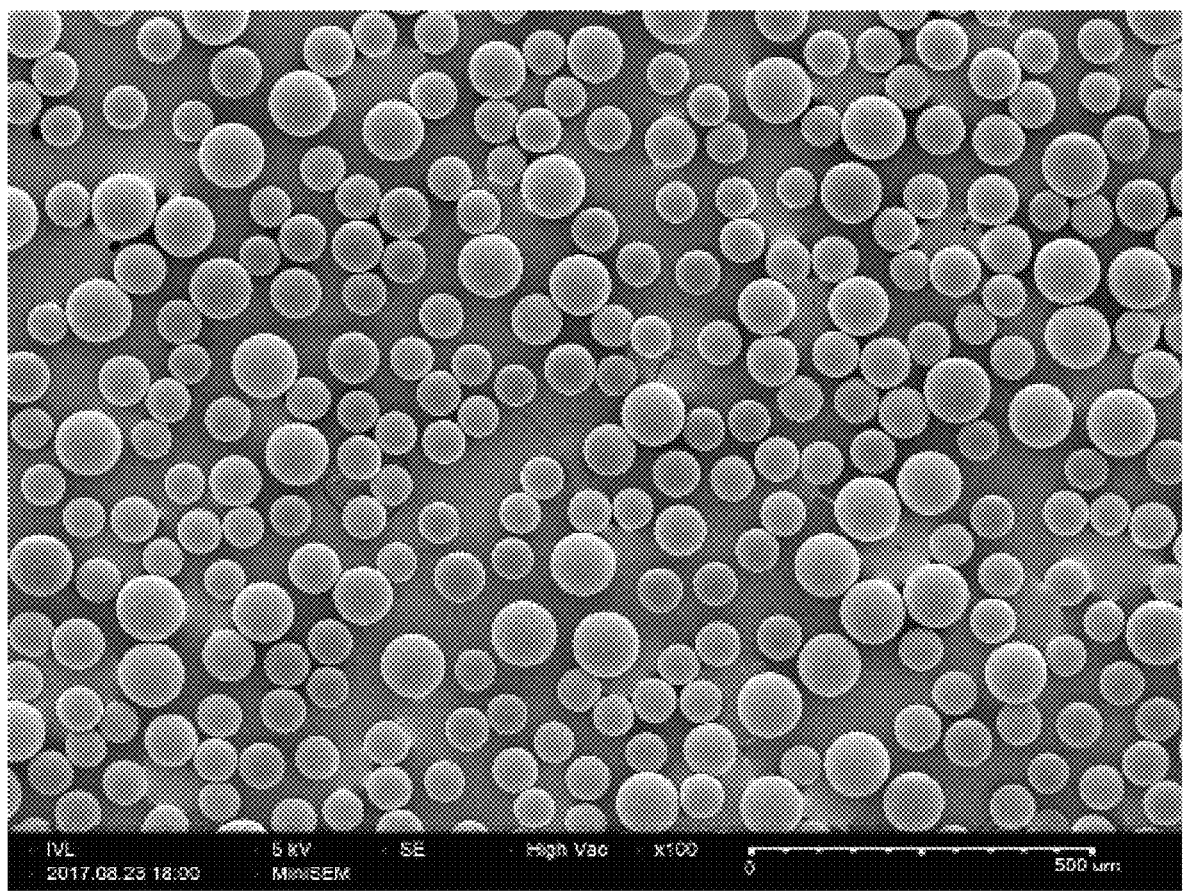
FIG. 6 is an SEM photograph of microparticles by the preparation method according to an exemplary embodiment of the present invention.
Figure 7:
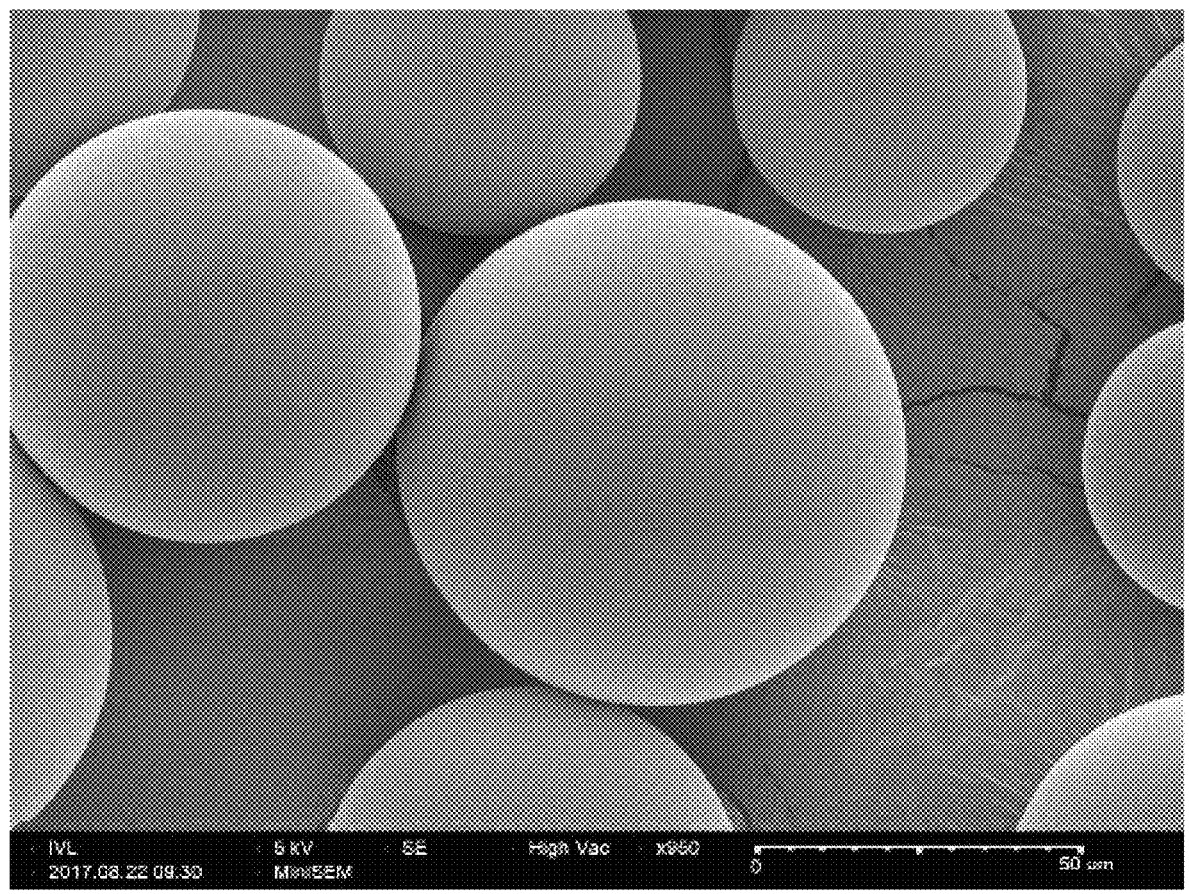
FIG. 7 is an SEM photograph of microparticles by the preparation method according to an exemplary embodiment of the present invention.

Δ means that due to the effect of the remaining solvent, an aggregation phenomenon of microparticles occurs and the shapes of the microparticles are not uniform as in the SEM photographs in FIGS. 4 and 5. On the contrary, in Examples 1, 10, and 11, it was confirmed that the shapes of the microparticles were uniformly formed, and the aggregation phenomenon did not occur as in the SEM photographs in FIGS. 6 and 7.

That is, during the stirring, it was confirmed that the temperature conditions affected the shapes of the microparticles and the occurrence of the aggregation phenomenon.

INDUSTRIAL APPLICABILITY

The present invention relates to microparticles containing finasteride and a preparation method thereof.

An object of the present invention is to provide sustained-release microparticles capable of maintaining the effect of treating alopecia sustainably for 1 month to 3 months when the microparticles containing finasteride are administered, unlike oral dosage forms in the related art, which need to be taken daily due to the short half-life, and a preparation method thereof.

Another object of the present invention is to provide ease in storage and handling because microparticles containing finasteride is used in a manner that the microparticles are administered to a patient through injection and the patient need not directly store and handle a medicine unlike oral dosage forms.

Still another object of the present invention is to maintain the effect of administering a drug for a long period of time such as 1 month to 3 months by using sustained-release particles containing finasteride, to, as an average diameter of particles is prepared to a constant micro size, maintain an effective drug concentration at a constant level by controlling the release of a drug from the microparticles, and to decrease a foreign body sensation and pain when the microparticles are applied to an injection consisting of particles with a uniform size and administered to a patient by the injection.

The invention claimed is:

1. A method for preparing microparticles comprising finasteride, the method comprising:
   1) preparing a first mixture by dissolving a biodegradable polymer and finasteride in an organic solvent;
   2) preparing a second mixture by dissolving a surfactant in water;
   3) infusing the first mixture in Step 1) into a microchannel in a straight-line direction and allowing the first mixture to flow;
   4) preparing microparticles in a form in which the finasteride drug is uniformly distributed in spherical biodegradable polymer particles by infusing the second mixture in Step 2) into a microchannel formed on both side surfaces or one side surface and allowing the second mixture to flow so as to form an intersection point with a microchannel through which the first mixture in Step 3) flows in a straight-line direction, and intersecting a flow of the first mixture in a straight-line direction with a flow of the second mixture;

5) collecting the microparticles produced at the intersection point in Step 4);

6) evaporating and removing an organic solvent present in the microparticles collected in Step 5) by stirring the microparticles; and 7) washing the microparticles in Step 6) and drying the microparticles, wherein the microparticles have an average particle diameter of 20 to 70 μm, wherein Step 6) comprises:

Step 6-1) firstly stirring the microparticles at a rate of 800 to 1,200 rpm at 14 to 16° C. for 1 to 2 hours;

Step 6-2) secondly stirring the microparticles at a rate of 800 to 1,200 rpm at 19 to 21° C. for 0.5 to 1.5 hours after the first stirring; and Step 6-3) thirdly stirring the microparticles at a rate of 800 to 1,200 rpm at 24 to 26° C. for 0.5 to 1.5 hours after the second stirring, wherein performing steps 6-1), 6-2), and 6-3) results in smooth surfaces of the microparticles.

2. The method of claim 1, wherein the first mixture in Step 1) comprises the biodegradable polymer in an amount of 10 to 20 wt %.

3. The method of claim 1, wherein the first mixture in Step 1) comprises the biodegradable polymer and the finasteride at a weight ratio of 4:1 to 15:1.

4. The method of claim 1, wherein the biodegradable polymer is selected from the group consisting of polylactic acid, polylactide, poly(lactic-co-glycolic acid), poly(lactide-co-glycolide) (PLGA), polyphosphazine, polyiminocarbonate, polyphosphoester, polyanhydride, polyorthoester, polycaprolactone, polyhydroxyvalerate, polyhydroxybutyrate, polyamino acid, and a combination thereof.

5. The method of claim 1, wherein the organic solvent in Step 1) is dichloromethane.

6. The method of claim 1, wherein the second mixture in Step 2) comprises the surfactant in an amount of 0.2 wt % to 0.3 wt %.

7. The method of claim 1, wherein Step 3) infuses the first mixture into a microchannel in a straight-line direction under a pressure of 600 to 1,000 mbar.

8. The method of claim 1, wherein Step 4) infuses the second mixture into a microchannel formed on both side surfaces or one side surface so as to form an intersection point with a microchannel through which the first mixture flows in a straight-line direction, and infuses the second mixture under a pressure of 1,200 to 1,600 mbar.

9. The method of claim 1, wherein Step 5) collects the microparticles in a bath comprising the second mixture.

10. The method of claim 1, wherein the microchannels in Steps 3) and 4 are formed on a surface of a wafer, and an average diameter of the microchannels is 40 to 100 μm.

* * * * *